(12) United States Patent
Litvinov et al.

(10) Patent No.: US 8,456,157 B2
(45) Date of Patent: Jun. 4, 2013

(54) NANOMAGNETIC DETECTOR ARRAY FOR BIOMOLECULAR RECOGNITION

(75) Inventors: Dmitri Litvinov, Houston, TX (US); Richard Willson, Houston, TX (US)

(73) Assignee: University of Houston, Houston, TX (US)

(*) Notice: Subject to any disclaimer, the term of this patent is extended or adjusted under 35 U.S.C. 154(b) by 818 days.

(21) Appl. No.: 11/996,945

(22) PCT Filed: Jul. 26, 2006

(86) PCT No.: PCT/US2006/029390
§ 371 (c)(1),
(2), (4) Date: Jan. 5, 2010

(87) PCT Pub. No.: WO2007/014322
PCT Pub. Date: Feb. 1, 2007

(65) Prior Publication Data
US 2010/0188075 A1 Jul. 29, 2010

Related U.S. Application Data

(60) Provisional application No. 60/702,865, filed on Jul. 27, 2005.

(51) Int. Cl.
*G01R 33/00* (2006.01)
(52) U.S. Cl.
USPC ............................ 324/214; 977/953; 977/958
(58) Field of Classification Search
USPC ................................... 324/214; 977/953, 958
See application file for complete search history.

(56) References Cited

U.S. PATENT DOCUMENTS 5,372,930 A * 12/1994 Colton et al. ................. 436/525
6,057,167 A    5/2000 Shieh et al.
2006/0019096 A1 * 1/2006 Hatton et al. ................. 428/364

OTHER PUBLICATIONS

Baselt, et. al., "A biosensor based on magnetoresistance technology," Journal/Biosens. Bioelectron., 13(7-8), pp. 731-739, 1998.
Wolf, et. al., "Spintronics: A spin-based electronics vision for the future," Journal/Science, 294(5546), pp. 1488-1495, 2001.
Childress, et. al., "Spin-valve and tunnel-valve structures with in situ in-stack bias," Journal/IEEE Trans. Magn., 38 (5), pp. 2286-2288, 2002.
Edelstein, et. al., "The BARC biosensor applied to the detection of biological warfare agents," Journal/Biosens. Bioelectron., 14(10-11), pp. 805-813, 2000.
Schotter, et. al., "Comparison of a prototype magnetoresistive biosensor to standard fluorescent DNA detection," Journal/Biosens. Bioelectron., 19(10), pp. 1149-1156, 2004.
Raab, A., et al., "Antibody recognition imaging by force microscopy," Nature Biotechnology 17, p. 902-905, 1999.
D'Souza, L.M., Larios-Sanz, M., Setterquist, R. A., Wilson, R. C., and Fox, G. E., "Small RNA Sequences are readily stabilized by inclusion in a carrier rRNA," Biotechnology Progress, 19, pp. 734-738, 2003.

* cited by examiner

*Primary Examiner* — Bot Ledynh
(74) *Attorney, Agent, or Firm* — Winstead PC

(57) ABSTRACT

A biomolecular sensor system includes an array of magnetoresistive nanosensors designed for sensing biomolecule-conjugated superparamagnetic nanoparticles. Materials and geometry of each sensor element are designed for optimized sensitivity. The system includes magnetic field generators to apply forces to superparamagnetic nanoparticles for 1) nanoparticle manipulation, 2) sensor magnetic biasing, 3) magnetic pull-off measurement for differentiation against non-specific association, and 4) removal of all particles from the sensor array surface.

23 Claims, 6 Drawing Sheets sensor top view sensor side view

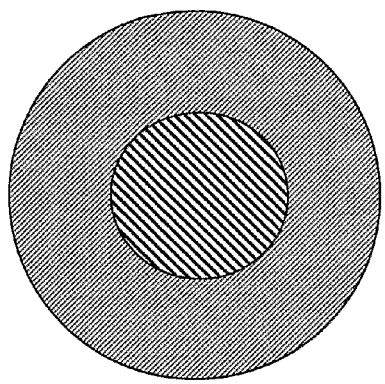
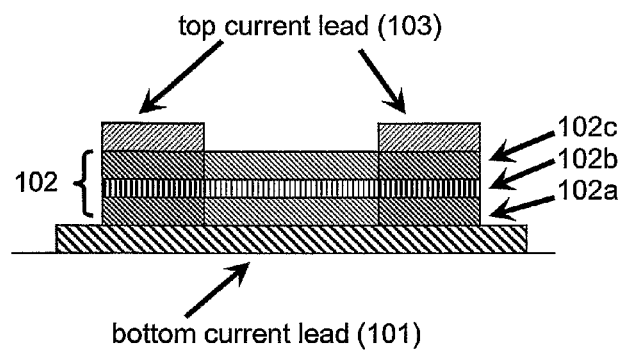
sensor top view
sensor side view
Fig. 1A
Fig. 1B

NANOMAGNETIC DETECTOR ARRAY FOR BIOMOLECULAR RECOGNITION

This application is a national stage of International Application No. PCT/US06/29390, filed on Jul. 26, 2006, which claims priority to U.S. Provisional Patent Application No. 60/702,865, filed on Jul. 27, 2005, which are incorporated herein by reference.

TECHNICAL FIELD

This invention relates to a biomolecular sensor system including an array of magnetoresistive sensors designed for sensing biomolecule-conjugated nanoparticles.

BACKGROUND OF THE INVENTION

The challenges in the growing field of high-throughput molecular screening (HTS) call for highly sensitive, economical, and massively parallel detector systems. Recent technology trends include the development of array assays for parallel detection of 100-100,000 species at a time, the rapid growth in the use of DNA probes for mRNA expression monitoring and sequence detection, and the advent of protein/antibody and cell arrays. These trends, which are expected to continue for the foreseeable future, call for transducers compatible with hybridization assays and molecular binding, implementable in dense array formats, with high sensitivity to target molecules. While HTS has experienced revolutionary changes over the past decade, speed and accuracy remain among the major challenges. For example, rapidly evolving fluorescent-label based instrumentation, which has proven to be highly useful in DNA sequencing and hybridization detection, can be prone to significant detection errors resulting from the possibility of massive summation of weak false interactions, photobleaching, and autofluorescence. There are also limitations of scanning speed and spatial resolution, and therefore array density and feature number. As noted in the NIH Molecular Libraries Screening Instrumentation program announcement, there exists a critical need to bridge the large gap between today's molecular screening capabilities and the requirements for advanced HTS technology.

The growing interest in high-content HTS-based on protein or gene expression monitoring, or the measurement of target/ligand binding in massively parallel fashion, calls for efficient, high-throughput molecular screening instrumentation. Quantitation of large numbers of biomolecular analytes is most commonly achieved through separation by electrophoresis, or by use of affinity binding agents such nucleic acid hybridization probes, antibodies or aptamers. In nearly all methods other than mass spectrometry, what is actually detected is a label of some sort, rather than the biomolecular analyte itself. In most applications, the sensitivity of detection of this label (rather than, e.g., kinetics or affinity agent binding tightness), limits assay performance.

The introduction of each successive generation of molecular labels has transformed the practice of biomolecular assays. With many exceptions, the general trend has been that enzymes, which are still widely used but which now have yielded important applications to fluorescent labels, largely supplanted radioisotopes. Fluors are widely and very successfully used, but detection sensitivity and signal stability remain important limitations. Single-molecule fluorescence detection is now reliably practiced, but only with elaborate equipment unsuited to most HTS applications. More importantly, fundamental optical limitations posed by triplet blinking and photobleaching impose major limitations on the detection performance that can be practically achieved with fluorescent labels.

The application of magnetoresistive sensors to biomolecular recognition was suggested by Shieh and Ackley in 1996 (Shieh and Ackley, "Magnetoresistance-based method and apparatus for molecular detection," U.S. Pat. No. 6,057,167) and first described in 1998 (Baselt et. al., "A biosensor based on magnetoresistance technology," Journal/Biosens. Bioelectron., 13(7-8), pp. 731-739, 1998). In this biodetection scheme, magnetic particles are used as labels for biological agents and are detected using magnetoresistive elements, where the resistance of a magnetoresistive sensor changes in the presence of a magnetic particle.

In a typical giant magnetoresistive (GMR) sensor, the resistance depends on the mutual orientation of two magnetic layers in a bi-layer structure. Two possible resistance-sensing configurations are possible: current in-the-plane of the sensor (CIP) and current perpendicular to the plane of the sensor (CPP). The resistance is the highest when the two layers are magnetized in opposite directions and is lowest when magnetizations are aligned in the same direction. Relative resistance change ($\Delta R/R$) values of 6-8% and 20-25% can be routinely obtained for CIP and CPP sensors, respectively, and can be measured in sub-100 nm magnetoresistive sensors to a precision of 0.1%, a signal-to-noise ratio of 100- to 250-fold (Wolf et. al., "Spintronics: A spin-based electronics vision for the future," Journal/Science, 294(5546), pp. 1488-1495, 2001; Childress et. al., "Spin-valve and tunnel-valve structures with in situ in-stack bias," Journal/IEEE Trans. Magn., 38(5), pp. 2286-2288, 2002). The presence of a magnetic particle disrupts the magnetic environment and under appropriate conditions may lead to a change in the sensor's resistance.

Considerable progress has been made in magnetic biosensor development (Edelstein et. al., "The BARC biosensor applied to the detection of biological warfare agents," Journal/Biosens. Bioelectron., 14(10-11), pp. 805-813, 2000; Schotter et. al., "Comparison of a prototype magnetoresistive biosensor to standard fluorescent DNA detection," Journal/Biosens. Bioelectron., 19(10), pp. 1149-1156, 2004) including the demonstration of bioconjugated magnetic multimicron-scale microbead detection using CIP GMR sensors and magnetic field removal (melting) of magnetic microbeads from the sensor surface for enhanced detection specificity. Magnetic "melting curves" are particularly promising as a means of improving the quality of hybridization and immunoassay data by discriminating against weak, non-specific interactions. Notably, magnetic removal curves are more compatible with heat-labile protein analytes, antibodies, cells and receptors than is thermal melting.

The limitations of magnetoresistive sensor and magnetic field source technologies have restricted the applications to the detection of magnetic microbeads (>2 μm, ca. 8000 times the mass and volume of those proposed for the present work) using relatively large magnetoresistive sensor elements. High magnetic-label-to-biomolecule size ratio can lead to reduced sensitivity, interference with biomolecular interactions, and highly multivalent, avidity-modified interactions, limiting the applicability of the technology.

Electrical and magnetic properties of larger magnetic sensor elements with dimensions of a micrometer and above are highly susceptible to small variations in sensor geometry making it necessary to significantly overdesign sensor array, for example, via introduction of select transistors, antiferromagnetic pinning layers and add-on current carrying coils to set the direction of magnetization. This limits the ability of the sensors to quantitatively analyze magnetic labels beyond distinguishing between "present" and "not present" events as well as making the sensors highly susceptible to external magnetic fields, which are necessary, for example, for the detection of superparamagnetic nanoparticles. Significantly, manipulation of superparamagnetic nanoparticles (such nanoparticles being a desirable choice for magnetic labels because of their unique magnetic properties) represents a major challenge as it requires generation of large magnetic field gradients not achievable with prior art macroscopic magnetic field sources. Moreover, quantitative magnetic field removal of magnetic labels has not been achieved. Magnetic field removal of particles held by a single biomolecular recognition interaction would be particularly informative. In addition, array feature density declines as the square of the magnetoresistive element size, reducing array density.

BRIEF DESCRIPTION OF THE INVENTION

In an effort to overcome the deficiencies in the above-described prior art, it is an object of this invention to enable nanomagnetic sensor system to allow the detection of sub-100 nm superparamagnetic nanoparticles and to quantitatively measure the bonding strength between biochemically-active surfaces of superparamagnetic nanoparticles and sensors.

It is further an object of this invention to produce nanomagnetic sensors with a self-imposed closed-loop magnetization state (or other unambiguously-defined magnetization state) that will not require sensor preconditioning and that will simplify sensor design, fabrication, and enable new analytical capabilities.

It is further an object of this invention to enable precise calibration of the sensor performance utilizing a nanomagnetic field source with the means of precise positioning of the field source over the sensor.

It is further an object of this invention to enable high magnetic field gradients for manipulation of sub-100 nm superparamagnetic nanoparticles.

It is further an object of this invention to build high magnetic field gradient sources for quantitative magnetic-pull off to enable precise measurements of the chemical bonding strength between a superparamagnetic nanoparticle and a sensor.

It is further an object of this invention to enable directed flow and delivery of superparamagnetic nanoparticles using high magnetic field gradient sources and microfluidic channels.

It is further an object of this invention to enable detection of the nature (i.e., type) and strength of one or a small number of molecular bonds between biochemically active surfaces of superparamagnetic nanoparticles and sensors.

It is further an object of this invention to build a sensor array system capable of data replication for improved data quality and to build large sensor arrays for simultaneous detection of multiple biochemical species.

It is further an object of this invention to utilize magnetic biosensor system for a number of applications including evaluating drug effectiveness, cancer biomarker detection, testing food safety, and bio-threat detection.

In some embodiments, the present invention is directed to a population of superparamagnetic nanoparticles, wherein at least 0.001 percent of the nanoparticles of said population are functionalized and comprise at least one biomolecular recognition species attached to their surface, and wherein at least 1 percent of the functionalized nanoparticles of said population comprise at most 1000 biomolecular recognition species covalently attached to their surface. In some such embodiments, the nanoparticles are magnetizable into an unambiguously defined magnetic states using an applied magnetic field of 1 Gauss to 5000 Gauss. In some such embodiments, the nanoparticles comprise a material selected from the group consisting of ferromagnetic and ferrimagnetic materials and combinations thereof. A preferred population of superparamagnetic nanoparticles comprises nanoparticles of superparamagetic iron oxide composition. Another preferred population of superparamagnetic nanoparticles comprises nanoparticles of superparamagetic cobalt ferrite composition. Another preferred population of superparamagnetic nanoparticles comprises iron oxide and/or cobalt ferrite and may also comprise a hydrophilic polymer.

In some of the above-described nanoparticle populations, the biomolecular species attached to any one of the magnetic nanoparticles that is functionalized is selected from the group consisting of proteins, nucleic acids, nucleic acid analogs, and combinations thereof. In some or other such "nanoparticle population" embodiments, a least some of the nanoparticles within said population comprising an outer coating. In some such embodiments, the outer coating comprises a material selected from the group consisting of gold, polymers, proteins, oxides and combinations thereof.

In some embodiments, the present invention is directed to a sensor array comprising: (a) a plurality of nanomagnetic sensing elements, wherein the sensing elements individually provide for less than 10 morphologically equivalent magnetization distribution states, by virtue of their nanometric size and corresponding nanomagnetic properties, and wherein electrical properties of said sensing elements vary in response to changes in applied magnetic environments, when such magnetic environments are applied; and (b) molecular recognition elements associated with at least 0.001% of the nanomagnetic sensing elements. In some such embodiments, the array comprises at least 100 nanomagnetic sensing elements. In some such embodiments, the nanomagnetic sensing elements comprise at least one nanomagnetic layer, wherein the local electrical properties of the sensing elements depend on local magnetization distribution.

In some such above-described sensor arrays, the nanomagnetic sensing elements possess a shape that is topologically equivalent to that of a torus. In some or other embodiments, these sensing elements are a disk and/or a C-shaped (i.e., crescent-shaped) object. In some or still other such embodiments, the nanomagnetic sensing elements possess a shape of an n-sided polygon wherein the number of sides is less than 10000. In some such embodiments comprising ring-like nanomagnetic sensing elements, the ring-like nanomagnetic sensing elements comprise an inner diameter of between 0.1 nm and 150 nm and a corresponding outer diameter of between 10 nm and 200 nm, and further comprise a height of between 1 nm and 100 nm.

In some such above-described sensor arrays, the molecular recognition elements reside closer than 100 nm to the center of the nanomagnetic sensing elements, and wherein, for those sensing elements containing molecular recognition elements, an average of no more than 5 such molecular recognition elements correspond to any one nanomagnetic sensing element within the array. In some or other such sensor arrays, the molecular recognition elements reside in the center of the nanomagnetic sensing elements, and wherein, for those sensing elements containing molecular recognition elements, an average of no more than 5 such molecular recognition elements reside in the center of any one nanomagnetic sensing element within the array. The nanomagnetic sensing elements comprise at least one nanomagnetic layer, wherein the local electrical properties of the sensing elements depend on local magnetization distribution.

In some such above-described embodiments, the nanomagnetic sensing elements comprise a material selected from the group consisting of anisotropic magnetoresistive materials, giant magnetoresistive multilayers for current-in-plane configuration, giant magnetoresistive multilayers for current-perpendicular-to-plane configuration, tunneling magnetoresistive multilayers, ballistic magnetoresistive material, and combination thereof. In some or other such embodiments, the nanomagnetic sensing elements comprise a material selected from the group consisting of materials exhibiting a Hall effect, materials exhibiting an extraordinary Hall effect, and combinations thereof.

In some such above-described sensor arrays, the molecular recognition elements are selected from the group consisting of proteins, antibodies, sugars, lipids, nucleic acids, nucleic acid analogs, and combinations thereof. In some or other such embodiments, the molecular recognition elements are associated with the nanomagnetic sensing elements via chemical (e.g., covalent and/or ionic) bonding. In some or other such embodiments, the molecular recognition elements are bound to lithographically-defined binding areas, in some or still other embodiments, the molecular recognition elements are bound to lithographically defined binding pads comprising gold, aluminum oxide, tantalum oxide, silicon oxide, and combinations thereof.

In some embodiments, the present invention is directed to a system for sensing comprising: (a) a nanomagnetic sensor array (as described above); (b) a population of superparamagnetic nanoparticles which are magnetizable into an unambiguously defined magnetic states using an applied magnetic field ranging from 1 Gauss to 5000 Gauss, wherein at least some of said superparamagnetic nanoparticles comprise biomolecular species covalently attached to their surface; and (c) a means for generating uniform magnetic fields, wherein at least some of biomolecular species on the superparamagnetic nanoparticles that comprise such species are capable of binding to at least some of the molecular recognition elements of the sensor array.

In some such above-described system embodiments, said system is operable for applying force to and propagating superparamagnetic nanoparticles. In some or other such embodiments, the superparamagnetic nanoparticles, in either a bound or unbound state, can be manipulated via magnetic fields. In some or other such embodiments, said system is operable for detection and quantitation of bio-molecular analytes. In some or other such embodiments, the system further comprises a microfluidics device. In some or other such embodiments, the means for generating uniform magnetic fields involves a device selected from the group consisting of a conductor coil, a solenoid, a solenoid with a magnetic core, and combinations thereof. In some or still other such embodiments, the binding between the biomolecular species and the molecular recognition elements comprises a linker species.

In some embodiments, the present invention is directed to a method comprising the steps of: (a) exposing a plurality of superparamagnetic nanoparticles to a nanomagnetic sensor array (see above), wherein at least some of the superparamagnetic nanoparticles have at least one biomolecular species bound to their surface; (b) permitting the biomolecular species on the superparamagnetic nanoparticles to conjugate with corresponding molecular recognition elements associated with the nanomagnetic sensing elements of the nanomagnetic sensor array so as to permit formation of a conjugated assembly; and (c) applying at least one magnetic field to manipulate at least some of the superparamagnetic nanoparticles.

In some such above-described method embodiments, at least some of the superparamagnetic nanoparticles are moved in a daisy chain fashion via selectively magnetizing magnetic elements. In some or other such embodiments, at least one magnetic field is uniform and is operable for magnetizing superparamagnetic nanoparticles for detection. In some or other such embodiments, the superparamagnetic nanoparticles have an average diameter of less than about 150 nm, and wherein the nanoparticles comprise a material selected from the group consisting of iron oxide, cobalt ferrite, cobalt, iron, and combinations thereof. In some or other such method embodiments, a linker species is employed to conjugate the superparamagnetic nanoparticles with the corresponding molecular recognition elements on the nanomagnetic sensor array.

In some such method embodiments, such methods further comprise a step of sensing conjugation between the superparamagnetic nanoparticles and the corresponding molecular recognition elements on the nanomagnetic sensor array by monitoring regional changes in electrical properties of said sensor array during application of a magnetic field suitable for magnetizing superparamagnetic nanoparticles. In some or other such embodiments, manipulation of the superparamagnetic nanoparticles with a magnetic field, coupled with changes in electrical properties of the sensor array, provides information about the conjugated assembly. In some or still other such embodiments, the magnetic field gradient removes at least some of the superparamagnetic nanoparticles.

In some embodiments, the present invention is directed to a nanoscale composite structure comprising: (a) a nanomagnetic sensing element comprising a bottom contact and a biomolecular recognition element positioned within the interior of the sensing element and attached to the bottom contact, wherein said sensing element comprises a material whose electrical properties vary in response to changes in applied magnetic environments, and wherein the sensing element provides for a single magnetic vortex, by virtue of its nanometric size and corresponding nanomagnetic properties, when such magnetic environments are applied; and (b) a functionalized superparamagnetic nanoparticle comprising at least one biomolecular species covalently attached to its surface, wherein exactly one such biomolecular species is conjugated to the biomolecular recognition element associated with the nanomagnetic sensing element.

In some such above-described embodiments involving a nanoscale composite structure, the nanomagnetic sensing element, when viewed topologically, is toroidal (or torus-shaped). In some or other such embodiments, the nanoparticle has a diameter of less than 100 nm. In some or other such embodiments, the biomolecular species is conjugated to the biomolecular recognition element via a linker species. In some or other such embodiments, the linker species is associated with the biomolecular species. In some or still other such embodiments, the bottom contact is gold.

In some embodiments, the present invention is directed to a method comprising the steps of: (a) exposing a plurality of superparamagnetic nanoparticles, said nanoparticles comprising at least one biomolecular species attached to their surface, to an object having a diameter at least 20 times the mean diameter of the nanoparticles, said biomolecular species being capable of interacting with at least one constituent of the object so as to form a nanoparticle-bearing object; (b) exposing the nanoparticle-bearing object to a nanomagnetic sensor array (see above), the sensor array having inter-sensor element spacing of not more than one-third of the longest dimension of the object; and (c) using responses from at least three sensor elements to characterize the location of at least two superparamagnetic nanoparticles interacting with the object.

In some such above-described method embodiments, the object is a cell of type selected from the group consisting of prokaryotic, eukaryotic, archeal, microbial, fungal, yeast, mammalian, and human. In some such embodiments, the cell is exposed to a stimulus selected from the group consisting of chemical, biological, environmental, and combinations thereof; and wherein the cell's response to said stimulus is assessed by comparison of patterns of magnetic signals from an array of nanomagnetic sensors. In some such embodiments, the cell contains DNA encoding an enzyme involved in the metabolic function of producing magnetic particles. In some such embodiments, the enzyme is expressed under control of regulatory elements different from those by which it is controlled in the organism in which it is naturally expressed.

In some embodiments, the present invention is directed to a method comprising the steps of: (a) attaching a plurality of superparamagnetic nanoparticles to a nanomagnetic sensor array by a tether of at least 10 nm in length to form a plurality of nanoparticle/tether combinations, wherein at least some of the nanoparticle/tether combinations comprise at least one biomolecular species; (b) exposing the plurality of nanoparticle/tether combinations to a molecular species operable for perturbing the biomolecular species of the nanoparticle/tether combination; and (c) measuring the sensor array's response to the perturbing species. In some such embodiments, the step of measuring is carried out in the presence of a field selected from the group consisting of a static electrostatic field, a time-varying electrostatic field, a static magnetic field, a time-varying magnetic field, and combinations and gradients thereof.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which:

FIGS. 1A and 1B illustrate plan (A) and side (B) views of a CPP GMR sensor design, in accordance with embodiments of the present invention;

DETAILED DESCRIPTION OF THE INVENTION

Figure 2:
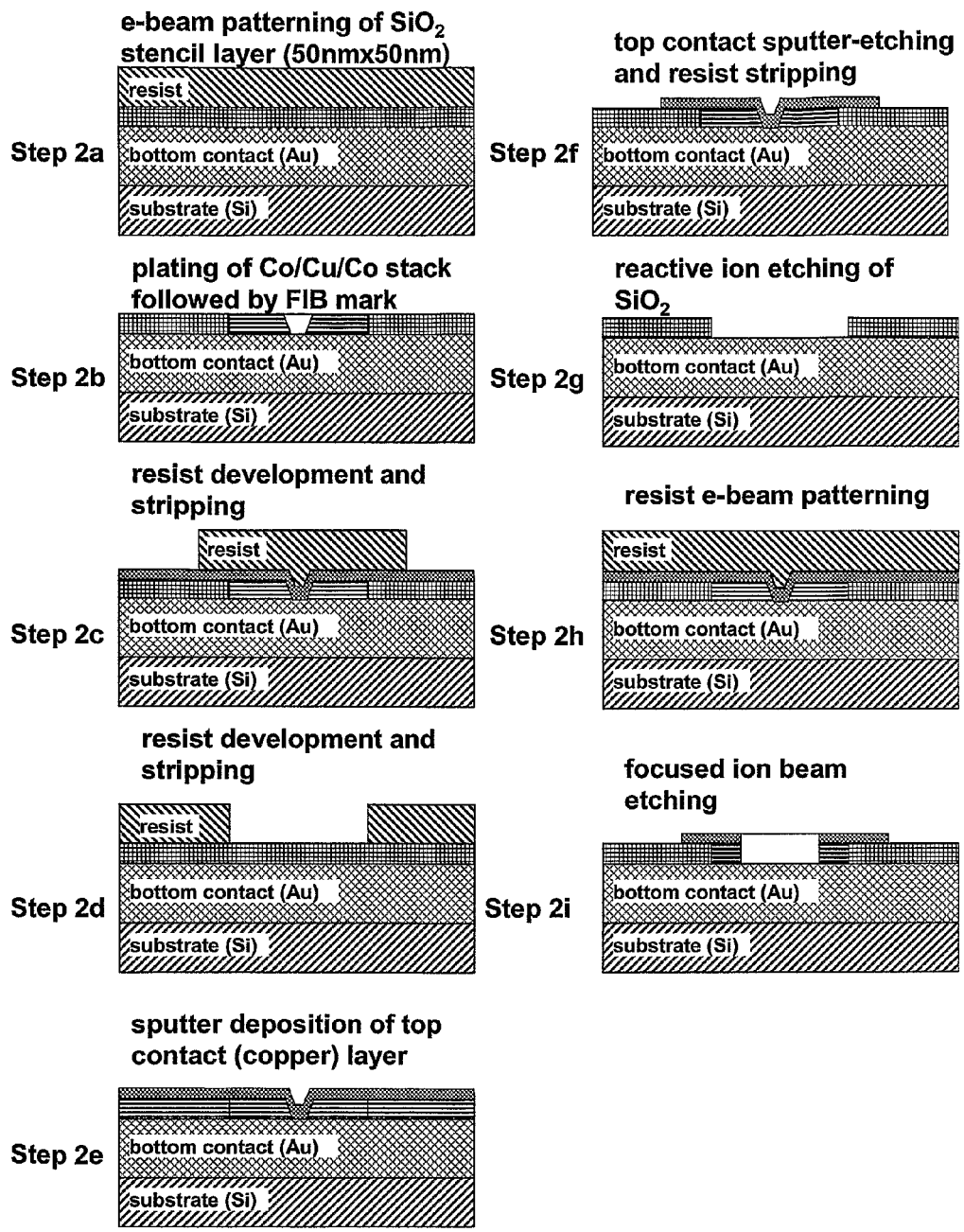
FIG. 2 illustrates, in stepwise fashion, a method of fabrication of a sensor array, in accordance with embodiments of the present invention.

In some embodiments, the present invention is directed to a biomolecular sensor system including an array of nanomagnetic sensors designed for sensing biomolecule-conjugated nanoparticles. Materials and geometry of each sensor element are designed for optimized sensitivity. The system includes one or more magnetic field generators to apply forces to superparamagnetic nanoparticles for 1) nanoparticle manipulation, 2) sensor biasing, 3) magnetic pull-off for the measurement of nanoparticles to sensor binding energies, and 4) removal of all particles from the sensor array surface.

In the following description, specific details are set forth such as specific quantities, sizes, etc. so as to provide a thorough understanding of embodiments of the present invention. However, it will be obvious to those skilled in the art that the present invention may be practiced without such specific details. In many cases, details concerning such considerations and the like have been omitted inasmuch as such details are not necessary to obtain a complete understanding of the present invention and are within the skills of persons of ordinary skill in the relevant art.

Referring to the drawings in general, it will be understood that the illustrations are for the purpose of describing a particular embodiment of the invention and are not intended to limit the invention thereto.

In some embodiments, the present invention includes a magnetic label sensor array, having an array of nanomagnetic elements whose electrical properties are affected by the magnetic environment. Nanomagnetic elements are patterned into structures with an opening for centering captured superparamagnetic nanoparticles and ensuring a reproducible magnetization state.

In some embodiments, a toroidal sensor geometry can be used, where a magnetoresistive GMR multilayer stack, for example, Co/Cu/Co, is patterned into a closed-loop structure, as illustrated in FIGS. 1A and 1B, and magnetoresistance is measured in current-perpendicular-to-plane (CPP) configuration. FIG. 1A illustrates a top-down (plan) view of such a toroidal sensor, and FIG. 1B illustrates cross-sectional side view of such a sensor, where a bottom current lead 101 supports multilayer stack 102 (102a=Co, 102b=Cu, 102c=Co), and where top current leads 103 are attached atop the multilayer stack. The toroidal design in the nanomagnetic regime supports only two stable magnetization states: clockwise and counterclockwise magnetic vortices. The thickness of the copper layer is optimized such that top and bottom cobalt layers are antiferromagnetically coupled that is the two magnetic layers have their magnetizations of opposite chiralities. For the purpose of nanoparticle detection the two possible states are identical, so no sensor pre-conditioning is required.

The toroidal sensor geometry allows several issues critical for reliable nanoparticle detection and simplified fabrication to be addressed. Firstly, the toroidal sensor design ensures a well-defined closed-loop magnetization distribution within each sensor, a critical aspect for achieving a well-defined, reproducible magnetic state in an unperturbed sensor. The self-imposed closed-loop magnetization distribution in such sensors allows significant simplification of the sensor design. Predictable closed-loop magnetization distribution is the direct result of nanoscale magnetic behavior where the characteristic device size is reduced to a length scale comparable to or smaller than the exchange length in the sensor material and would generally not be possible in larger magnetic device structures. Additionally, the design maximizes the change in the magnetization distribution in the presence of a particle, thus improving sensitivity. Additionally, only the bottom of the sensor center opening is functionalized. A label is fitted to the center opening to bind to the sensor surface. This ensures precise positioning of superparamagnetic labels, critical for detection signal reproducibility. Additionally, the field gradients created by the sensor guide the nanoparticles towards the sensor center, thus improving efficiency.

In some or other embodiments, various other closed-loop geometries of magnetoresistive sensor can be used to achieve nanoparticle centering and pre-defined magnetization states. For example, ring, oval, square, pentagon, hexagon, or a n-sided structures with a center opening can support stable well-defined states such as various morphologies of a closed-loop magnetization state. The center opening of circular shape is preferred due to simplified fabrication. Other shapes such as square, pentagon, hexagon, or a n-side opening would enable the same functionality.

Magnetoresistive stacks based on Co/Cu/Co multilayers in a CPP configuration are preferred due to simplified fabrication and detection methodology. Application of other CPP GMR sensors such as CoFe/Cu/CoFe, Co/Cu/NiFe, CoFeNi/Cu/CoFeNi, NiFe/Cu/NiFe with additional inclusion of pinning layers such as FeMn, IrMn or synthetic antiferromagnets such as Co/Cu/Co or Co/Ru/Co are also contemplated. Magnetoresistive sensors based on CIP GMR, tunneling magnetoresistance (TMR) such as Co/Al$_2$O$_3$/Co, Fe/MnO/Fe, CoFe/MnO/CoFe, ballistic magnetoresistance (BMR), anisotropic magnetoresistance, or Hall-effect can be used as well.

The sensitivity to nanoparticle presence is dramatically enhanced via the application of a biasing magnetic field, preferably perpendicular to the sensor surface. In the absence of a magnetic label (superparamagnetic nanoparticle), such a biasing field will have a negligible effect on the magnetization distribution as long as it is substantially smaller than the demagnetizing field of ~4πM$_S$ (M$_S$ is the saturation magnetization of the sensor magnetic material). For example, in CoFe based bi-layer sensors 4πM$_S$ is ~20 kGauss (kG), thus, an external field of less than ~1-2 kG will have minimal impact on magnetic configuration and, consequently, on magnetoresistance (the Earth's ambient magnetic field is about 5 Gauss).

In a typical mode of operation, if a 1 kG vertical biasing field is applied and the following material parameters are assumed: magnetization saturation M$_S$=8×10$^5$ A/m, exchange constant A=1×10$^{-11}$ J/m, and anisotropy field H$_K$=5 Oe, the presence of a 50 nm superparamagnetic γ-Fe$_3$O$_4$ nanoparticle will lead to a change in the resistance of up to ~70% of the total ΔR/R range. Fitting the nanoparticle into a center hole helps maximize the out-of-plane magnetization rotation and, consequently, maximize the expected sensitivity.

The nanoparticle detector (i.e., the sensor array) is adapted as a superior biomolecular sensor, using superparamagnetic nanoparticles as labels, so as to form a detection system comprising a sensor array and superparamagnetic nanoparticles (labels), wherein at least some of the superparamagnetic nanoparticles are attached to biomolecular species. The surface of the sensor's small center opening is functionalized with a molecular recognition element (e.g., a DNA probe or antibody), allowing either direct, sandwich or competitive assay formats (only the bottom of the opening is functionalized; see assembly details in FIG. 1B. Nanoparticles nonspecifically attached to the sensor surface can be removed from the sensor surface by application of a magnetic field and the remaining nanoparticles are sensitively detected by the change in magnetoresistance.

Magnetic field sources with controllable spatial variations of magnetic field and magnetic field gradients are an integral part of the sensor array system and also are essential for the characterization of individual magnetoresistive sensor elements. Such magnetic field sources can be either built from commercially-available conventional magnetic recording heads, which are readily available in a variety of magnetic configurations, or from the ground-up using conventional lithography techniques. Focused ion-beam technology is used for fine alterations of the recording heads either to achieve spatially uniform field gradients for magnetic pull-off or to build ultra-small field generators for individual sensor characterization. Alternatively, magnetic field sources can be built from ground up using conventional integrated circuit technology.

Nanoparticles are larger than the biomolecules of interest, but are so small as to be diffusible, Brownian particles (volume comparable to small viruses, and mass less than that of a bacterium). Upon application of a magnetic field gradient, a biomolecule labeled with a superparamagnetic nanoparticle will diffuse towards the sensor. Stoke's Law can be used to estimate the terminal velocity, v, of a superparamagnetic nanoparticle (label) pulled by the magnetic force $F_H$=M·dH/dz toward the sensor surface in the presence of a viscous drag force $F_d$=6πμvd, where M is the magnetic moment of the label, d—its diameter, and μ is the liquid viscosity. The expression for the terminal velocity is given by v=(m$_S$d$^2$/36μ)(dH/dz), where M$_S$ is the magnetic saturation moment per unit volume of the superparamagnetic label material. In water (μ=0.0089 Poise at 25° C.), a 50 nm iron oxide particle (M$_S$~100 emu/cm$^3$) will reach a terminal velocity of about 7 mm/sec in the presence of a field gradient of 10 Oe/nm. Considering the high density of features on the array, this velocity is more than sufficient to greatly enhance sensor performance. Spin-dependent electronic properties of magnetic multilayers have been successfully utilized in magnetic data storage for the past 10 years. Utilized for superparamagnetic nanoparticle detection, the sensor will be biased with a small (~100 Oe) uniform in-plane magnetic field (easily achievable with a set of small Helmholtz coils) to ensure high-resistance anti-parallel configuration of magnetic layers. As discussed above, the presence of a superparamagnetic nanoparticle will disrupt the high-resistance state, which can be accurately detected using simple electronics.

FIG. 2 schematically illustrates an example of the sensor array fabrication flow. Referring to FIG. 2, e-beam lithography is used to define the sensor lateral geometry in a polymethylmethacrylate (PMMA) resist and transferred into 20 nm thick SiO$_2$ using CHF$_3$ reactive ion etching (Steps 2a-2c). Magnetoresistive (Co/Cu) multilayers are electrodeposited into 50 nm diameter openings in the SiO$_2$ from a single sulfate electrolyte containing Co$^{2+}$ and Cu$^{2+}$ ions using potentiostatic control (Step 2d). Electrochemical deposition has proved to be a reliable sensor synthesis tool to achieve high values of magnetoresistance while simplifying some of the processing issues associated with materials synthesis by sputtering. The bottom contact is made of gold (1) to enable gold/thiol attachment of the capture probes at the bottom of the center opening and (2) to improve the quality of the electrodeposited (Co/Cu) multilayer stacks by preventing contact surface oxidation. The center opening in the magnetoresistive sensor is formed using focused ion-beam (FIB) (Step 2d). FIB is well suited to patterning nanomagnetic devices because the higher mass-to-charge ratio of the Ga$^+$ ions makes the technology minimally susceptible to the relatively strong magnetic fields often present in the vicinity of magnetic devices. Ga$^+$ ion implantation during focused ion-beam milling leads to some magnetoresistance reduction due to layer intermixing at the edges of the milled region; however, the effect is relatively small since only at most 10-15% of the sensor is affected. Prior to FIB milling, the entire circuit is coated with an ultra-thin (5 nm) hydrogenated carbon (C:H$_X$) overcoat for corrosion protection. Similar coatings are used in disk drive manufacturing to protect the recording heads and media. The inner walls of the center opening are coated in a separate processing step with a thin protective layer of carbon using oblique deposition from a Kaufman ion source. Cu is then sputter-deposited as a top contact layer (Step 2e). Additional resist deposition, patterning, development and etching is then carried out to pattern the top Cu contact (Steps 2f-2h). Finally, the FIB milling is then subjected to FIB etching to expose the underlying gold surface in the center for biomolecule immobilization by thiol-gold chemistry (Step 2i).

Figure 3:
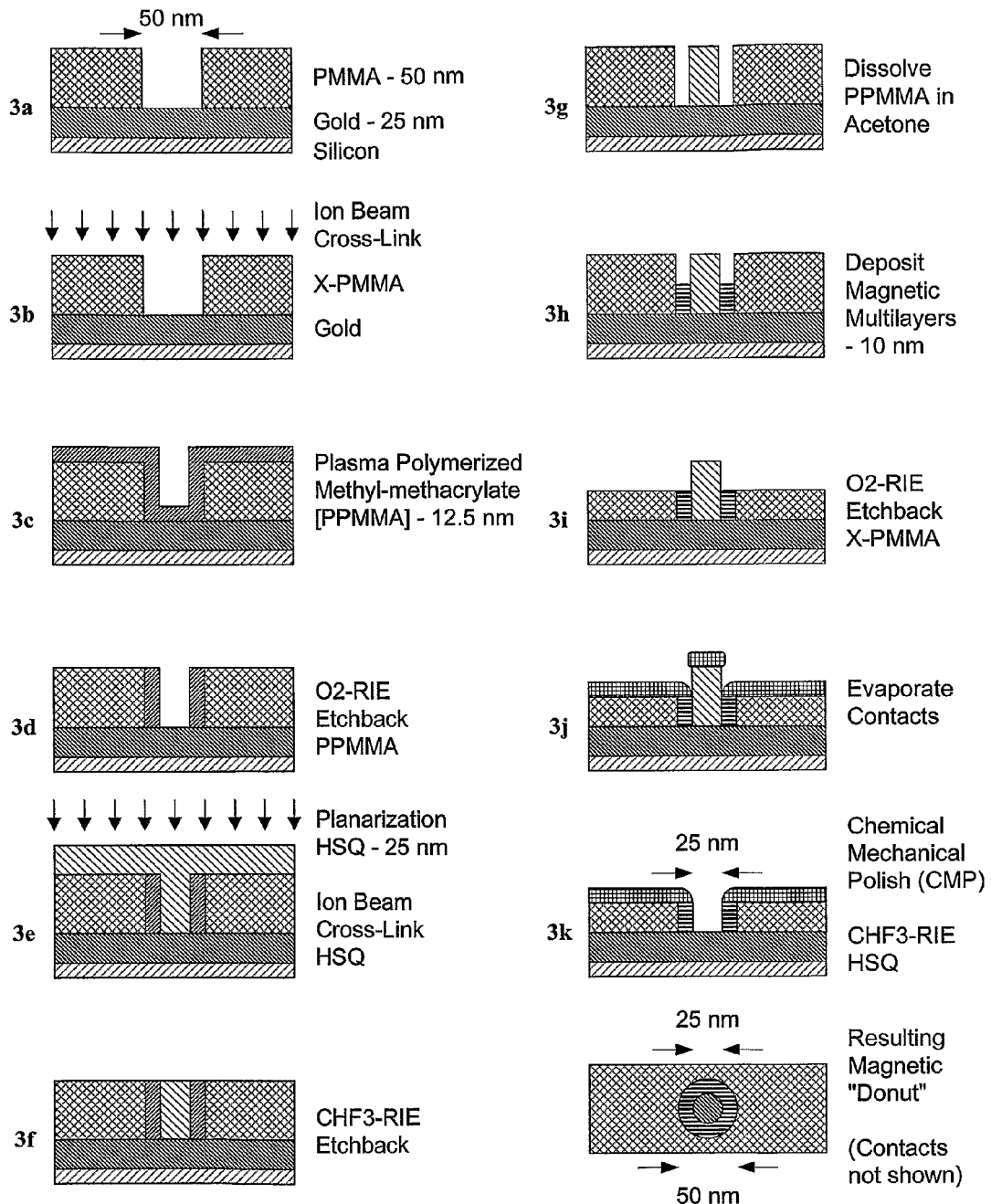
FIG. 3 illustrates, in stepwise fashion, a more efficient method of fabrication of a sensor array, in accordance with embodiments of the present invention.

FIG. 3 schematically illustrates an exemplary and preferred method of the sensor array fabrication flow. In Step 3a, a thin gold film is sputter deposited, with a titanium adhesion layer (not shown) on a silicon substrate and coated with a 50 nm thick layer of poly(methylmethacrylate) (PMMA) resist. Electron beam (e-beam) lithography is then used to form an array of circular openings, 50 nm in diameter. In Step 3b, the PMMA film is cross-linked (X-PMMA) by proton bombardment rendering it insoluble in acetone with a (+) shows the fraction of resist remaining after a 30 second development in acetone as a function proton and electron dose with a proton dose of about $2\times10^{-4}$ C/cm$^2$ is adequate for this purpose. In Step 3c, a conformal polymer coating is deposited by plasma-enhanced CVD using methylmethacrylate feedstock. This coating of plasma-polymerized (methylmethacrylate) (PPMMA) is deposited in such a fashion as to prevent in situ cross-linking by plasma electrons utilizing magnetic field to deflect incident electrons away from the wafer. PPMMA can be selectively removed in acetone while X-PMMA remains untouched. PPMMA structures are cross-linked by ion beam proximity lithography and developed in acetone to remove the unexposed material. This image shows exposed and developed lines running over anisotropically etched V-grooves in silicon. This exemplary process relies on the conformality of the coating and its selective dissolution in acetone. In Step 3d, reactive ion etching with oxygen feedstock (O$_2$-RIE) removes a uniform layer from the surface of the sample. The etch is anisotropic, removing the coating on the planar surfaces without etching the sidewalls. In Step 3e, hydrogen silsesquioxane (HSQ), a resist containing a high concentration of silica, is spun on the sample. The recess is filled and the surface planarized. The resist is then cross-linked by proton exposure with a dose of $5\times10^{-6}$ C/cm$^2$. This is insufficient to cross-link the PPMMA, which just begins to cross-link at $2\times10^{-4}$ C/cm$^2$. In Step 3f, HSQ is etched back to expose the resist by RIE with a CHF$_3$ feedstock (CHF$_3$-RIE). In Step 3g, PPMMA is selectively dissolved in acetone. Neither X-PMMA, nor cross-linked HSQ is removed in this process. In Step 3h, magnetic multilayers are electroplated into the mold from a single sulfate electrolyte containing Co$^{2+}$ and Cu$^{2+}$ ions using potentiostatic control. In Step 3i, the X-PMMA is recessed using O$_2$-RIE forming an HSQ pillar. In Step 3j, electron beam evaporation is used to deposit the aluminum top contact. In Step 3k, the HSQ post is removed by chemical, mechanical polish (CMP), a standard process in integrated circuit manufacturing. Finally, the HSQ is removed by CHF$_3$-RIE, revealing the Au layer to which the probes will bind. This step will not attack the aluminum metallization. The readout lines are then masked and etched by Cl$_2$/BCl$_3$-RIE. The resulting magnetic "donut" is illustrated in the plan view shown in Step 3l.

Figure 4:
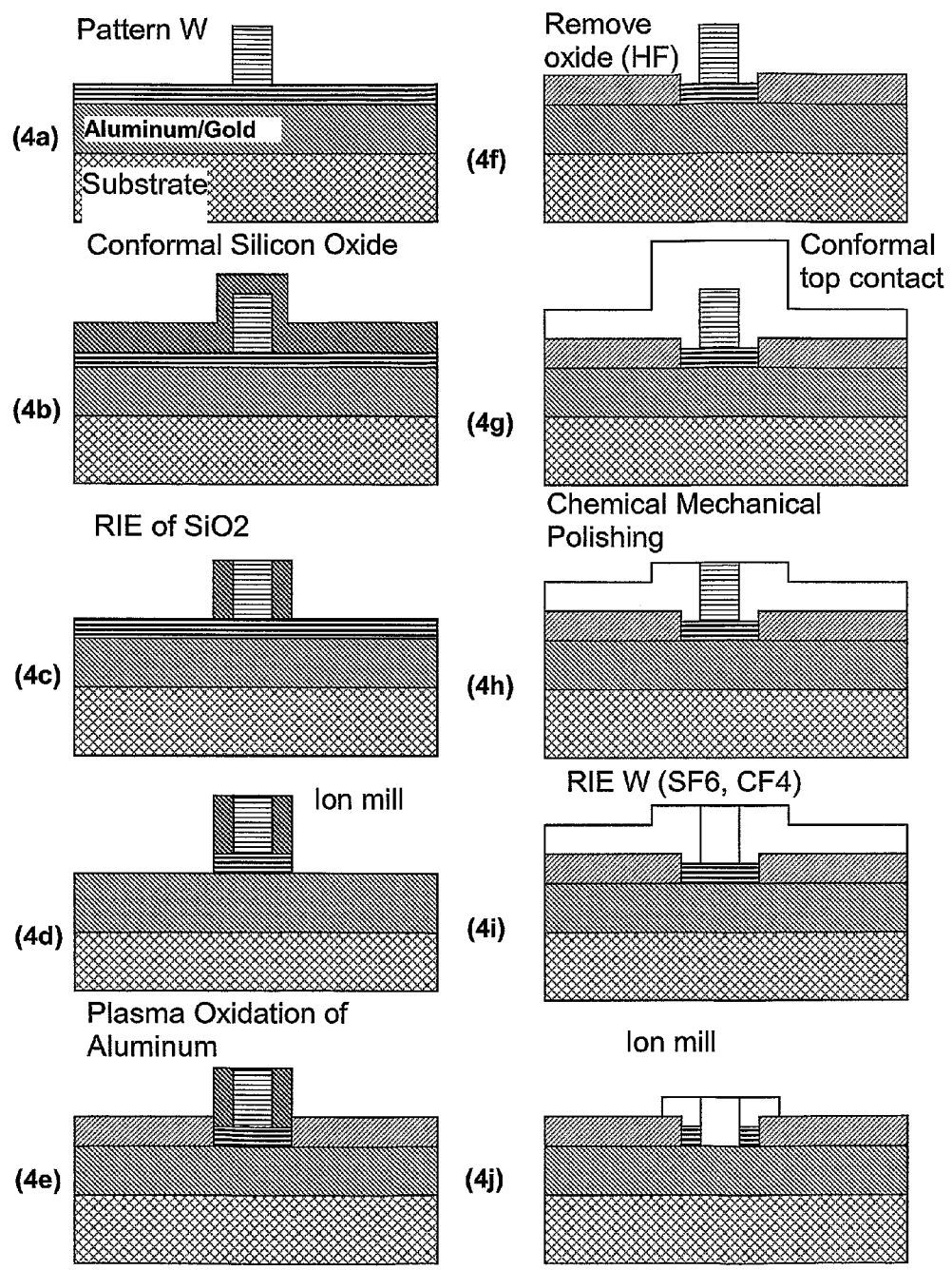
FIG. 4 illustrates, in stepwise fashion, a preferred method of fabrication of a sensor array, in accordance with embodiments of the present invention.

FIG. 4 schematically illustrates a preferred method of the sensor array fabrication flow. Referring to FIG. 4, an aluminum/gold bottom contact coated with sensor material is deposited and patterned using e-beam lithography. This is followed by e-beam lithography step to pattern a tungsten (W) hard mask where the W hard mask defines the center opening of the sensor element (Step 4a). A conformal coating of silicon oxide (SiO$_2$) is deposited next by sputtering followed by reactive ion etching (RIE) of SiO$_2$ in CHF$_3$ (Steps 4b-4c). This step forms the sensor hard mask. The structure is ion-milled to define external dimensions of the sensor elements where unmasked sensor materials is removed along with the thin gold layer covering aluminum bottom contact (Step 4d). Aluminum is oxidized in oxygen plasma to form aluminum oxide (Al$_2$O$_3$) which will serve as an insulator between the top and the bottom contacts (Step 4e). The SiO$_2$ hard mask is removed in brief exposure to HF vapor or in highly diluted HF acid. Top copper contact is deposited conformally by sputtering followed by chemical mechanical polishing step to expose W hard mask (Steps 4f-4g). W hard mask is etching using reactive ion etching in SF$_6$ or CH$_4$ (Step 4i). The last step removes sensor materials in the center of the sensor element and patterned the top contact using ion-milling (Step 4j).

The means for minimizing the influence of stray electric fields include grounding of both the solution-exposed electrode and the test solution. The remainder of the sensor array surface is electrically-insulated from the solution with an insulating coating including by not limited to hydrogenated carbon, aluminum oxide, tantalum oxide, and silicon oxide. The estimated thickness of the electrical double layer on the inner walls of the sensor elements is less than 2 nm (top electrode is biased at 10 mV). It follows that nearly the entire area above the gold surface is at ground potential. Also, the only electrochemically-active surface exposed to the solution is the bottom electrode, which is at the same potential (ground) as the solution. No electrochemical reactions are expected to take place. Also, the voltages used will be in the few mV range, far too low to drive electrochemical reactions of concern. For example, water hydrolysis requires a voltage of at least 1,230 mV, much higher than those to be used here.

Hydrogenated carbon (C:Hx) and diamond-like carbon (DLC) overcoats can be used for corrosion and mechanical wear protection. The C:Hx and DLC surface is less protein-adsorptive than graphite and is actually quite hemocompatible (e.g., Jones et al., "Protein adsorption and platelet attachment and activation on TiN, TiC, and DLC coatings on titanium for cardiovascular applications," J. Biomed. Mater. Res. 52(2), pp. 413-421, 2000), but still adsorbs protein to some extent. Proteins (and nanoparticles) adsorbed on the overcoat film will be away from the active sensor areas or at least far off-center, in an area in which the sensor is much less sensitive. In the event that further passivation of the inactive surface is required, several options can be pursued including but not limited to: 1) the surface can be readily passivated by adsorption of an inert layer (e.g., the commonly-used BSA, or for better control a hydrophobic/PEG block copolymer); 2) the DLC layer can be replaced or overcoated with aluminum dioxide deposited by evaporation/oxidation of aluminum (angularly to avoid coating the bottom of the hole at the active center of the sensor).

High quality pin-hole free aluminum oxide (alumina, sapphire) overcoat is highly insulating and is readily achievable by oxygen plasma oxidation of a thin aluminum layer, which will be deposited non-conformally by evaporation at an angle (to avoid coating of the gold active surface of the sensor) in an ultra-high vacuum deposition system available to us (deposition and film quality are somewhat superior to silica, which would also be an option). Importantly, aluminum dioxide can be activated with primary amines by standard aminosilane chemistry (e.g., Azour et al., "Fourier transform infrared spectroscopic characterization of grafting of 3-aminopropyl silanol onto aluminum/alumina substrate," Spectrochim Acta A Mol. Biomol. Spectrosc., 56A(8), pp. 1627-1635, 2000) to allow coupling of hydrophilic polymers (e.g., the N-hydroxysuccinimide (NHS) ester of a PEG carboxylic acid, Nektar product 2M4K0D01, or shorter-chain aminoPEGs from Biovectra, or similar products now available from Quanta Biodesign) for superior surface passivation.

In some embodiments of the present invention, sensor array calibration is achieved via utilization of a local field source (probe head) mounted on an XYZ 3D nanomanipulator. The field source is used to address individual sensor cells with sub-1 nm position accuracy and to locally alter the magnetic state of the cells while probing the sensor's resistance. Designed with a 40 nm cavity/void at the air-bearing surface for remnant magnetization suppression, the probe head generates a negligible magnetic field unless the magnetizing coils are energized (0-200 mA). The ability to accurately position the field source over the sensor surface, to vary the field strength and the field profile provides an unprecedented testing capability for magnetoresistive sensor evaluation and is an invaluable tool for superparamagnetic label sensor design and development. The probe can also be used as a magnetic tweezers for accurate magnetic label positioning over the sensor while measuring the sensor's electrical response. This capability is used to test the superparamagnetic label sensing capabilities of the sensor elements and to evaluate signal errors in events of misregistration of superparamagnetic labels with respect to the sensor center (e.g. due to defects in the sensor or superparamagnetic label geometries), and the effects of standoff due to the presence of biomolecules on the superparamagnetic nanoparticle and sensor surfaces.

While mRNA/cDNA detection is a potentially important application of the nanomagnetic biosensor, Applicants have initially employed hybridization of an oligodeoxyribonucleotide analog of positions 7-25 of the 5S rRNA of *Vibrio proteolyticus* to a complementary DNA sequence (and designed mismatches to test specificity). This is not only a well-characterized model system, but is a direct test of the superparamagnetic nanoparticle biosensor's performance in DNA probe-based mRNA expression analysis and SNP scoring.

Applicants have extensively characterized anti-lysozyme antibodies and continue to use them in their research on the biophysical chemistry of molecular recognition. Applicants have determined the titration calorimetric enthalpies and entropies of association in these systems, as well as the on- and off-rates of the HyHEL-5 and HyHEL-10 antibodies with Hen Egg and avian variant lysozymes. Applicants have also cloned and expressed in *E. coli* the antigen-binding Fab fragment of HyHEL-5, and collaborated on the crystallographic determination of the Protein Database PDB-deposited structure of this molecule in complex with the lysozyme antigen. One of the antibodies of interest has also been characterized by atomic force microscopic (AFM) characterization of single-molecule binding events (A. Raab, W. Han, D. Badt, S. J. Smith-Gill, S. M. Lindsay, H. Schindler, P. Hinterdorfer, Nature Biotechnology 17, p. 902, 1999).

AFM pull-off recognition studies provide an excellent control on the magnetic pull-off, as the superparamagnetic nanoparticle resembles an AFM tip, and the pull-off force-sensitivity of the molecular interaction can be directly compared with the magnetic "melting" and force/distance measurements possible with the superparamagnetic nanoparticle biosensor.

The *Vibrio proteolyticus* rRNA sequences used as model systems have been extensively used in Applicants' prior NASA- and EPA-sponsored work on microbial detection and labeling by insertion of stable engineered 5S rRNA molecules displaying detectable "guest" sequences. (D'Souza, L. M., Larios-Sanz, M., Setterquist, R. A., Willson, R. C., and Fox, G. E., "Small RNA Sequences are readily stabilized by inclusion in a carrier rRNA," *Biotechnology Progress*, 19, pp. 734-738, 2003).

Magnetic particles, which are sufficiently small to exhibit superparamagnetic behavior, are preferred. In superparamagnetic particles, stored magnetic anisotropy energy is smaller than the energy of thermal fluctuations such that the magnetic moment is frustrated that is has no preferred orientation. Such particles are magnetically very soft and easily magnetized by the application of small external magnetic fields. Magnetite ($Fe_3O_4$) particles with sub-100 nm size are preferred for their environmental stability, relatively high magnetic moment of 62 emu/gram, and superparamagnetic behavior. Other superparamagnetic nanoparticles can be used as well including, but not limited to, Fe, Co, FeCo, cobalt ferrite, and others.

Methods for the attachment of biomolecules, such as peptides, proteins, and DNA to gold sensor surface are well established. Reactive functional groups include primary amines, carboxylic acids, alcohols, and thiols. Applicants coupled both thiol-displaying antibody Fab' (antigen-binding Fab-like fragment, proteolytically cut to display a free cysteine thiol) fragments and (commercially-obtained) thiolated DNA on gold sensor surfaces. Another such attachment method is one in which a thioether bond is formed via the reaction of a biomolecule-bound thiol group with a nanoparticle-bound maleimide group. If needed, amide-coupling reactions can also be used, where carbodiimides or sulfo N-hydroxysuccinimide esters are used to catalyze the reaction between primary amines and carboxylic acids to form stable amide bonds.

For immobilization of biomolecules on nanoparticles, species such as, but not limited to, avidin-, dextran-, streptavidin-, goat anti-mouse- and anti-fluorescein antibody-modified superparamagnetic nanoparticles can be used. Biotinylated oligonucleotides are widely commercially available, and can be used. Immobilization of antibodies use carbodiimide activation of dextran and goat anti-mouse as immediately implementable for use in the biosensor testing. Subsequently, Fab' fragments can be immobilized through their free —SH functionalities as described above. DNA bearing free thiol- or amino-functionalities added during standard commercial solid-phase synthesis can also be immobilized using similar chemistries. In some cases it is possible to monitor the extent of coupling by release of a chromophore as part of the coupling reaction. In other cases, coupling can be monitored by directly assaying the immobilized biomolecule (e.g., using the Pierce bicinchoninic acid BCA assay for Fab protein], which liberates a soluble, diffusible chromophore, or in some cases by total organic carbon), or by liberating the bound molecule (e.g., by chemical or enzymatic hydrolysis), removing the particles and assaying the liberated compounds (e.g., by UV/visible absorbance, amino acid analysis, or total organic carbon.

The concentration (and fraction) of functional biomolecules can be assayed by control experiment binding of fluor-labeled lysozyme (for Fab) or complimentary oligonucleotide (for DNA probes). It may be possible to measure fluor concentration even in the presence of moderate nanoparticle-induced scattering, using, for example, a SPEX 212 fluorometer with dual emission grating monochrometers and Glan-Thompson polarizers for scattered light rejection (or other similar device). Should this prove difficult, bound HEL/oligo target can be eluted non-destructively (low pH or high temperature, respectively), beads removed magnetically, and the eluted partner measured. To ensure that elution is quantitative, a control mass balance can be calculated by comparing the amount eluted to the amount removed from the supernatant during the binding process (the particle/oligo ratio used during loading is adjusted to keep the removed fraction reliably measurable). The fraction of immobilized biomolecules competent for binding may be improved by the use of longer spacer arms in the coupling agent (dozens are commercially available). The density of immobilization can also be varied; the sensor is expected to give single-particle/single-molecule sensitivity, but can also be operated with multiple biomolecules per particle or per sensor.

In addition to binding competence, the selectivity of binding by the immobilized Fab/DNA probe can be tested by competitive adsorption of sub-optimal targets (Bobwhite quail lysozyme and mutant oligo target, respectively). Both direct binding, sandwich and competitive binding assays are attainable and the elimination of signal by steric hindrance due to a target bound to a particle-associated probe can also be used.

The aggregation properties of the biomolecule-derivatized particles (unloaded and loaded with lysozyme or target oligo) can be measured using light scattering. The suspension stability of the modified nanoparticles typically is equal to or exceeds that of the unmodified particles.

The sensor (sensor array) is incorporated into a temperature-controlled flow system for application of test materials. While shear torques on nanoparticles are very small, potential effects of flow on nanoparticle capture is controlled and, if necessary, quiescent binding or magnetic assist will be used. Well-characterized model systems for which Applicants know the biophysical characteristics (both kinetic and equilibrium; see above) are used to test the sensitivity and minimum useful binding affinity of the sensor, with the goal of demonstrating single-molecule sensitivity. While transport limitations are difficult to control for in solid-phase binding assays in complex geometries, the slow off-rates of tight binders can be accurately measured by flooding the system with unlabeled competitors, and these results can be directly compared with our previously-determined off-rates from kinetic fluorescence anisotropy. Inverting the affinity pairs (by immobilizing the partner previously soluble in solution) will provide a good control on any chemical and steric effects of immobilization.

Figure 5:
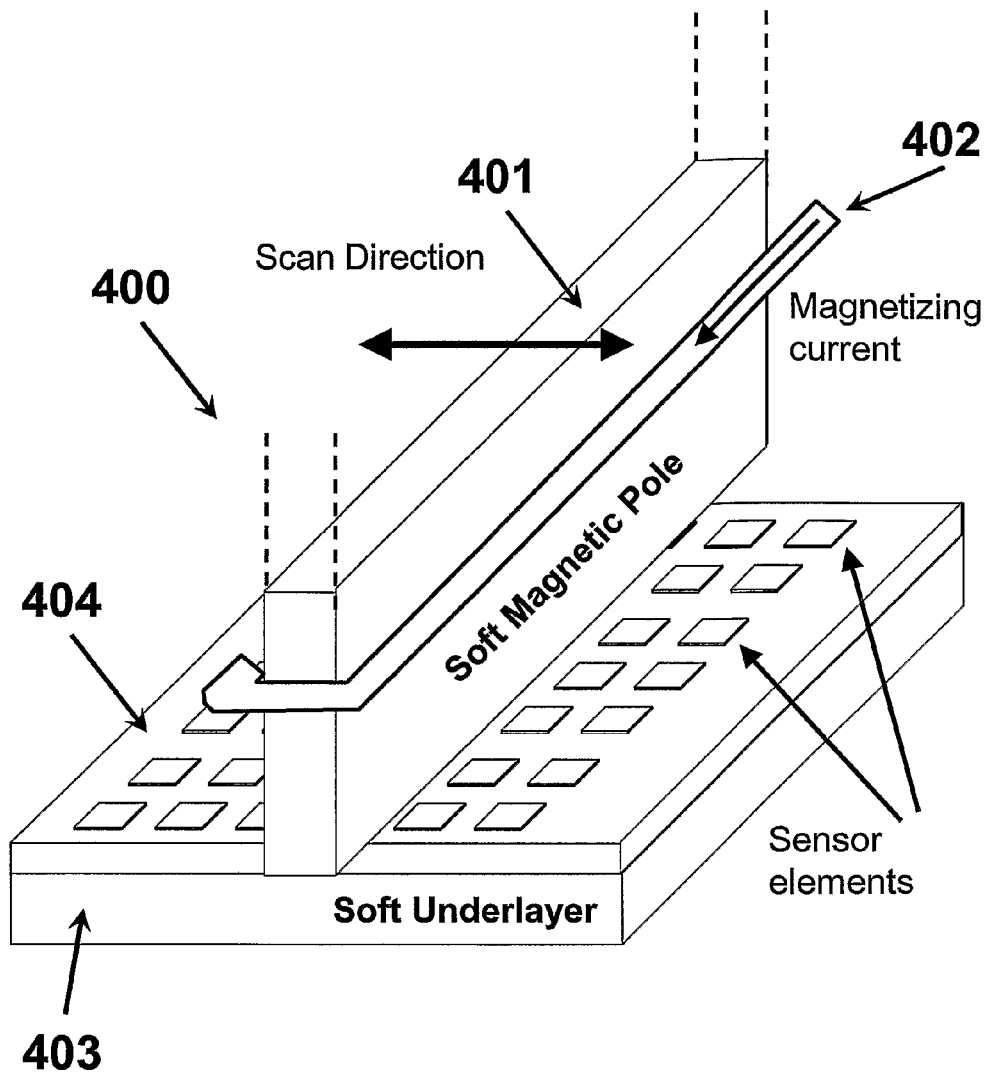
FIG. 5 depicts a magnetic pull-off sub-system, in accordance with embodiments of the present invention.

The strength of chemical bonding between a nanoparticle and functionalized surface of the detector cell can be tested by applying an external magnetic field to pull the particles off the surface while monitoring the sensor's electrical properties. FIG. 5 schematically illustrates an exemplary magnetic pull-off sub-system 400 and includes a magnetic field source for generating high magnetic field gradients comprising a soft magnetic core 401 and a magnetizing coil 402. The soft magnetic core can be built from a variety of soft magnetic metals and alloys including, but not limited to, Ni, Co, Fe, NiFe, CoFe, CoNiFe, CoZrNb, CoZrTa, FeAlN, FeTaN, and alloys of the above to include noble metals such as Pd, Pt, Ir, Rh, Au, transition metals such as Sm, Gd, Tb, Dy, Ho and other elements such as Cu, Ag, B, Ta, Zr, Nb, Cr. A preferred material for the magnetizing coil is Cu. The design may also include a soft magnetic underlayer 403, beneath sensor array 404, to control magnetic field profiles. The soft magnetic underlayer can be built of soft magnetic metals and alloys such as, but not limited to, Ni, Co, Fe, NiFe, CoFe, CoNiFe, CoZrNb, CoZrTa, FeAlN, FeTaN, and alloys of the above to include noble metals such as Pd, Pt, Ir, Rh, Au, transition metals such as Sm, Gd, Tb, Dy, Ho and other elements such as Cu, Ag, B, Ta, Zr, Nb, Cr.

Several magnetic pull-off sub-system designs are possible. For example, a point magnetic source for pulling one particle at a time off an individual sensor and scanned in x-y to address individual sensors. A linear source, as in schematics below (preferred design), that pulls nanoparticles from several sensors and is linearly scanned across the sensor array to cover all the sensors. A large source that pulls all nanoparticles from all sensors simultaneously, and combinations and variations of the above.

A broken bond and removal of the nanoparticle from the sensor will result in a change of the sensor electrical properties. Typical variations in bonding energy variations detected are in 0.1 eV (or 2 kcal/mole) ranges assuming a 50 nm nanoparticle, a 20 Oe/nm field gradient (readily achievable using magnetic recording head technology), and 10 kG saturation magnetization of the nanoparticle material (e.g., iron oxide). Magnetic pull-off melting can be used to measure bonding strength and to discriminate against non-specifically associated particles, enhancing the quality of the sensing results. In addition, particles anomalously tightly bound due to multi-molecule polyvalent avidity effects can be readily identified and these results discounted. Magnetic pull-off extends the data quality-enhancement of temperature melting curves from nucleic acids to other, more temperature-labile systems.

Variations in superparamagnetic nanoparticle (label) size lead to the variations of the pulling force and the measured bonding strength. One percent variation of the label diameter contributes to an approximately 3% variation in the detected bonding strength. Nevertheless, these label size variations will also affect magnetoresistance and, since each sensor element can be addressed individually, the label size variations can be relatively easily corrected. Relatively monodisperse labels are still quite desirable for simplified detection.

Magnetic pull-off also allows for simultaneous monitoring of multiple species, e.g. mixed mRNA/cDNA samples from different sources, in a manner similar to the common Cy3/Cy5 fluorescent imaging method. Labeling of target molecules from the two sources of interest with particles differing either in size or magnetic properties allows separate quantitation of targets from the two sources. This strategy typically involves the use of a large number of separate sensors, but the potential for enormous parallelization is a major feature of the nanomagnetic sensor array of the present invention.

The magnetic pull-off source is designed so as to generate a uniform field gradient across the sensor array to ensure a uniform pulling force. As the field gradient is increased, the superparamagnetic labels that are simply adsorbed to the sensor surface leave the sensor array first (and their departures will be individually detected in real time) followed by the labels attached via weak non-specific bonds. Due to the heterogeneity of non-specific binding, the superparamagnetic label removal will occur over a range of field gradient values up to some critical value when only specifically bound labels remain. When the field gradient reaches the value sufficient to break specific bindings, all the labels leave the sensor array nearly simultaneously. Magnetic melting curves, i.e. the dependence of superparamagnetic label binding sensed by the sensor array on the applied magnetic field gradient, are collected and serve as a primary molecular recognition tool.

Temperature and magnetic field can both be used to "melt off" oligo hybridization (pH and magnetic field for antibody/antigen association). Temperature melting curves of the standard *Vibrio proteolyticus* 5S rRNA system are prepared by standard hypochromism and compared with the Tm determined in the sensor. Comparison of reductions in hybridization temperature upon introduction of mismatches is used as a test of specificity, and to assess the effects of coupling chemistries, spacers, etc. This data is then compared with magnetic-field melting curves to demonstrate increasing information content, with considerably less effort than required for determination of temperature melting curves by classical methods.

In some embodiments, it is also possible to extract force-distance curves, like those from AFM experiments, but in a massively parallel manner. This can be achieved with the use of highly monodisperse superparamagnetic particles (produced as described above, possibly with additional magnetic and/or chromatographic fractionation for extreme uniformity). With the knowledge of the GMR response from individual sensors as a function of particle offset derived from the nanopositioning probe experiments described above, and possibly with individual and/or parallel sensor calibration experiments to correct for any inter-sensor variations in sensitivity, it is possible to infer the separation distance between the nanoparticle and the sensor surface from the GMR signal. Thus, using the present invention, it possible to routinely establish a strong, uniform, and well-calibrated magnetic field across the sensor surface for magnetic pull-off, and sets of (GMR data vs. magnetic field) points are then transformed into force-distance curves such as are produced by AFM, but in a massively parallel manner.

Figure 6:
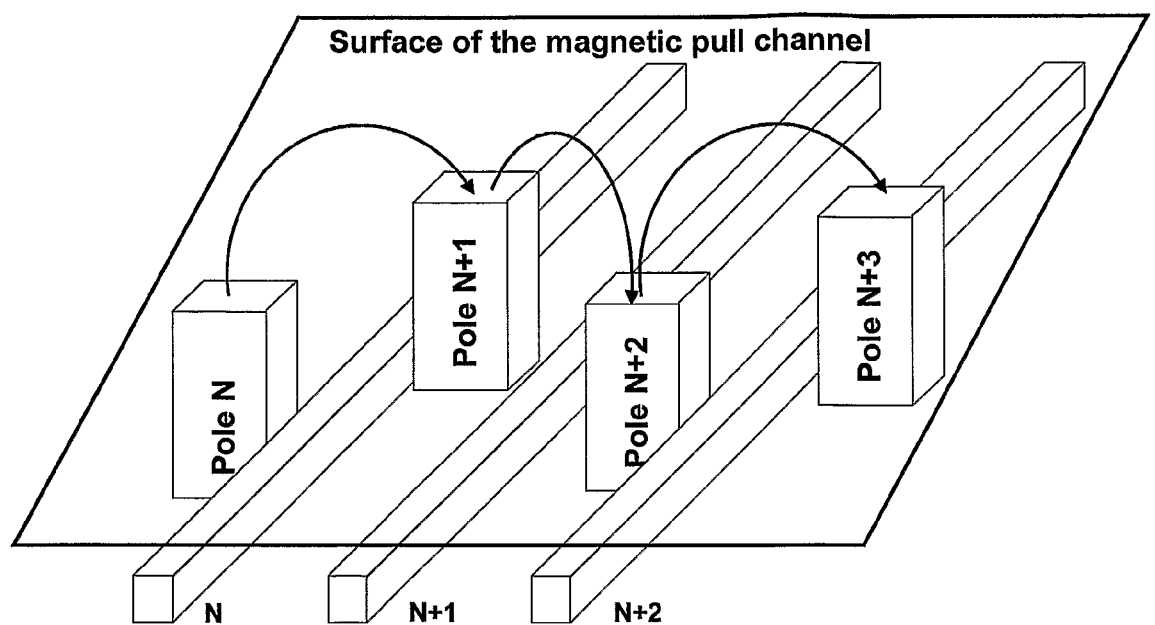
FIG. 6 depicts superparamagnetic nanoparticle manipulation using an array of magnetic field sources, in accordance with embodiments of the present invention.

Expanding on the above, an array of magnetic field sources can be used to directionally manipulate the flow of superparamagnetic nanoparticles. In the schematic of the magnetic pull array shown in FIG. 6, magnetic poles N, N+1, N+2, etc. are sequentially vertically magnetized using pairs of magnetizing wires N−1 and N, N and N+1, N+1 an N+2, etc., respectively, to cause the motion of superparamagnetic nanoparticles from N to N+1, than N+1 to N+2, etc. The current in adjacent magnetizing wires runs in opposite directions. The entire magnetic drive assembly is buried under the surface of the magnetic pull channel. This approach can be useful in positioning and/or selecting particles, cells, etc., before, during or after analysis.

While many samples such as mRNA/cDNA are relatively "clean," a key advantage of the sensor of the present invention is its robustness to the practical challenges of performing assays on complex biological samples such as culture media and cell lysates. It is inherently resistant to turbidity and optical scattering, and is compatible with the use of hydrolysis-resistant modified nucleic acid analogs, and blocked and non-natural peptides. Perhaps most importantly, all sample-exposed surfaces can be coated with biocompatible materials without degradation of performance. One approach is the application of a (self-assembling, and highly adsorption-resistant) coating of commercial short-chain PEG to the gold-coated surfaces of both the sensor and the nanoparticles.

The sensor array system can be used in various applications including cancer biomarker detection, evaluation of drug effectiveness, food safety, biothreat detection, and others.

In cancer diagnostics, the magnetic sensor array system can be applied to test breast cancer markers including estrogen receptor (ER) and HER-2, especially in ultra-small size samples such as those obtained by fine needle aspiration biopsy. ER is the most important growth factor identified for breast cancer. Normal breast tissue and benign breast lesions characteristically lack the receptor protein, which appears to be induced in neoplastic cells during mammary carcinogenesis. HER-2 is a type I receptor tyrosine kinase that is overexpressed in 20-25% of human breast cancers. Several clinical trials are currently evaluating therapies to inhibit proliferation of breast cancer via the HER-2 pathway. Several clinical studies and experimental models have demonstrated an inverse relationship between HER-2 overexpression and ER expression. The cross-talk between the HER-2 and ER signaling pathways forms the basis for clinical trials combining ER- and HER-2-targeted therapies.

The magnetic nanosensor can be used to test breast cancer markers including estrogen receptor (ER) and HER-2, the clinical importance of which was described above. For this application, fine needle aspirate samples from breast cancer patients can be used. Total RNA extracted from MCF-7 (ER-positive and negative for HER2) and SK-BR-3 (which overexpresses HER-2 and does not express ER) cell lines will be used as positive and negative controls for different protein markers.

In drug screening applications, the sensitivity and high density of the array allows higher-throughput screening, using smaller amounts of materials. Single-molecule sensitivity and large numbers of sensors improve data quality.

Numerous variations exist with regard to the above-described embodiments. These variations are summarized in Table 1 below.

TABLE 1

Extensions and modifications of major parameters.

| Parameter | Variation |
| --- | --- |
| Superparamagnetic nanoparticle material | Hematite, enzyme-generated, recombinant cell-generated, enzymatically-modified, self-assembling, magnetite, cobalt, iron oxide, cobalt ferrite, iron, nickel, iron platinum, iron palladium and various ferromagnetic and ferromagnetic alloys and composited |
| Magnetic Field Source material | Ni, Co, Fe, NiFe, CoFe, CoNiFe, CoZrNb, CoZrTa, FeAlN, FeTaN, and alloys of the above to include noble metals such as Pd, Pt, Ir, Rh, Au, transition metals such as Sm, Gd, Tb, Dy, Ho and other elements such as Cu, Ag, B, Ta, Zr, Nb, Cr |
| Coating layer on particle/detector binding pads | Gold, silver, Aluminum, Platinum, Nickel, silicon oxide, iron oxide, PEG oligomers, PEG, dextran, anticorrosion coating, carbohydrate, enzyme substrate, SAM, |
| Coating layer for detector expluding binding pads | Diamond-like carbon, hydrogenated carbon, aluminum oxide, tantalum oxide, silicon nitride, silicon oxide, hydrogen silsesquioxane (HSQ), SAM |
| Assay modality | Direct binding, sandwich, competitive displacement, kinetic, Friguet, indirect, melting curve, parallel, magnetic pull-off, cell motions, cell motility, cell population assay, cell dynamics, high-throughput, enzyme inhibition, presence/absence, quantitative, pattern formation, differential, comparison to reference |
| Target to be detected | Cell surface receptor, protein, nucleic acid, mRNA, genomic DNA, PCR product, cDNA, peptide, hormone, drug, spore, virus, SSU RNAs, LSU-rRNAs, 5S rRNA, spacer region DNA from rRNA gene clusters, 5.8S rRNA, 4.5S rRNA, 10S RNA, RNAseP RNA, guide RNA, telomerase RNA, snRNAs -e.g. U1 RNA etc, scRNAs, Mitochondrial DNA, Virus DNA, virus RNA PCR product, human DNA, human cDNA, artificial RNA, siRNA, micro RNA, Bacterium, virus, plant, animal, fungus, yeast, mold, Archae; Eukyarotes; Spores; Fish; Human; Gram-Negative bacterium, *Y. pestis*, HIV1, *B. anthracis*, Smallpox virus, Chromosomal DNA; rRNA; rDNA; cDNA; mt DNA, cpDNA, artificial RNA, plasmid DNA, oligonucleotides; PCR product; Viral RNA; Viral DNA; restriction fragment; YAC, BAC, cosmid, hormone, drug, pesticide, digoxin, insulin, HCG, atrazine, anthrax spore, explosive, sarin |

TABLE 1-continued

Extensions and modifications of major parameters.

| Parameter | Variation |
|---|---|
| Sample | Blood sample, air filtrate, tissue biopsy, cancer cell, surgical site, soil sample, water sample, whole organism, spore, genetically-modified reporter cells, Body Fluids (blood, urine, saliva, sputum, sperm, biopsy sample, forensic samples, tumor cell, vascular plaques, transplant tissues, skin, urine; feces); Agricultural Products (grains, seeds, plants, meat, livestock, vegetables, rumen contents, milk, etc.); soil, air particulates; PCR products; purified nucleic acids, amplified nucleic acids, natural waters, drinking water, contaminated liquids; surface scrapings or swabbings; Animal RNA, cell cultures, pharmaceutical production cultures, CHO cell cultures, bacterial cultures, virus-infected cultures, microbial colonies, drug candidate, combinatorial library, drug candidate mixture |
| Sample preparation agent | acid, base, detergent, phenol, ethanol, isopropanol, chaotrope, enzyme, protease, nuclease, polymerase, helicase, adsorbent, ligase, primer, nucleotide, restriction endonuclease, detergent, ion exchanger, filter, ultrafilter, depth filter, multiwell filter, centrifuge tube, multiwell plate, immobilized-metal affinity adsorbent, hydroxyapatite, silica, zirconia, magnetic beads |
| Sample preparation method | Filter, Centrifuge, Extract, Adsorb, protease, nuclease, partition, wash, leach, lyse, amplify, denature/renature, electrophoresis, precipitate, germinate, Culture |
| Utility | Clinical Diagnosis; Pathogen discovery; Biodefense; Research; Gene expression, Adulterant Detection; Counterfeit Detection; Food Safety; Taxonomic Classification; cell biology, drug candidate screening, Microbial ecology; Environmental Monitoring; Agronomy; Law Enforcement |
| Assay format | Chip, microfluidic device, Flow injection analysis, cell culture support surface, Well plate, filter, immunochromatographic assay, immunoassay, hybridization assay, biopsy specimen, in situ in patient, in surgical incision, surface, cell surface, thin section, self-assembled array |
| Molecular Recognition element on sensor or superparamagnetic particle | Antibody, nucleic acid, carbohydrate, aptamer, ligand, chelators, peptide nucleic acid, locked nucleic acid, backbone-modified nucleic acid, lectin, sugar, lipid, receptor, viral protein, mixed, cDNA, microRNA, enzyme, cell, cell surface protein, virus |
| Immobilization chemistry | Avidin/biotin, amine, carbodiimide, thiol, gold/thiol, metal chelate affinity, aldehyde, antibody, hybridization |
| Size of particle or sensor | 3 nm-3 mm |
| Number of sensors per array | 1-100,000,000,000 |
| Number of sensors per recognition element | 1-100,000,000,000 |
| Surface coating | Antibody, nucleic acids, PEG, dextran, protein, SAM, alkanethiol, peptide, polymer, polyol |
| Detector type | GMR, GMR array of 2-100,000,000,000 elements, current in-the-plane of the sensor, current perpendicular to the plane of the sensor, TMR, BMR, various magnetic alloy compositions such as Co, Ni, Fe, CoFe, CoNiFe, NiFe, various non-magnetic spacer compositions such as Cu, Al$_2$O$_3$, Ru, MnO, and geometries such as torus, disk, C-shape or crescent, square, pentagon, hexagon, n-sided shape with various opening shapes such as circle, square, pentagon, hexagon, n-sided opening. |
| Sensor materials | GMR or TMR multilayer of AF1/FM1/NM/FM2/AF2 configuration where AF1 and AF2 are single of multilayers of antiferromagnetic materials with various compositions, designs, and number of individual sub-layers such as FeMn, IrMn, NiMn, PtMn, iron oxide or synthetic antiferromagnets such as Co/Ru/Co and combinations of the above where AF layers are optional; FM1 and FM2 are single or multilayers of ferromagnetic metals or alloys such as Co, Fe, Ni, CoFe, NiFe, CoNiFe, CoAlN, CoFeN, CoZrNb, CoZrTa; NM is a non-magnetic layers such as Cu, aluminum oxide, boron nitride, manganese oxide. |
| Read-out and reporting method | Wireless, crossed-wire grid, independent lead to individual sensors, off-the-chip electronics, on-the-chip electronics, for examples, integration on top of a CMOS integrated circuit, computer-controlled for reliability statistics accumulation and data analysis |

The following examples are included to demonstrate particular embodiments of the present invention. It should be appreciated by those of skill in the art that the methods disclosed in the examples that follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

EXAMPLES

Example 1

Direct, mRNA Assay mRNA is isolated from a thyroid biopsy specimen, fragmented, and conjugated to superparamagnetic nanoparticles bearing short oligonucleotide linkers using RNA ligase. Less than 20% of the particles bear more than one linker, so that most mRNA molecules are the only ones on their particles. The nanoparticle-mRNA conjugates are exposed to an array of GMR sensors of which the majority bear a single LNA (locked nucleic acid) probe directed to target sequences potentially found in the mRNA. After hybridization, a magnetic field is used to remove un-conjugated and mis-hybridized particles, bound particles are detected, and a stronger field is used to remove correctly-hybridized particles. Particles are again detected, and hybridization which resists the lower field but not the stronger field is interpreted as evidence of the presence of specific mRNA sequences. The presence and absence of specific sequences is used to diagnose the patient's condition.

Example 2

Tethered Particle Assay

An array of GMR sensors, of which the majority bear a single gold-thiol-bound thiolated DNA oligonucleotide, is exposed to soluble oligodeoxynucleotides which can hybridize with those on the sensor, each of which is attached to a superparamagnetic nanoparticle by avidin-biotin chemistry, to give an array of nanoparticle-bearing, largely double-stranded DNA strands on the GMR sensor array. The GMR signal from each sensor is recorded, optionally in the presence of a magnetic field or field gradient. A sample containing transcription factors potentially capable of binding to some of the double-stranded DNA constructs is added, and the GMR signals are again recorded, optionally in the presence of a magnetic field or field gradient. Changes in the GMR signals associated with some DNA sequences are interpreted as evidence of the presence of transcription factors capable of binding to those sequences.

Example 3

Tethered Particle—Alter Tether

A set of oligodeoxynucleotides whose sequences each include 8 copies of a particular 23-nucleotide sequence are immobilized by spotting onto an array of nanomagnetic sensors. Each oligo is spotted onto 50 sensors, on average, and sensors bearing oligonucleotides carry an average of 1.05 oligonucleotides. Avidin-conjugated nanomagnetic particles are washed over the array and allowed to couple to biotin molecules on the distal end of the oligonucleotides. The output of each nanomagnetic sensor is repeatedly monitored, and its average strength, as well as statistical measures of its variability and autocorrelation are recorded.

A sample containing microRNAs complementary to some of the oligonucleotide repeat sequences is incubated with the array, while an oscillating magnetic field gradient is applied to promote mass transfer. The array is washed, and the strength, variability and autocorrelation of the GMR sensors' output signals are again recorded. The array is washed at a higher temperature, and the GMR signals again recorded. Changes in the GMR signals of sensors bearing certain oligonucleotide sequences are interpreted as signaling the presence of microRNAs complementary to those sequences.

Example 4

Tethered Particle—Alter Tether, Probe with Varying Magnetic Field

A set of oligodeoxynucleotides whose sequences each include 8 copies of a particular 23-nucleotide sequence are immobilized by spotting onto an array of nanomagnetic sensors. Each oligo is spotted onto 50 sensors, on average, and sensors bearing oligonucleotides carry an average of 1.05 oligonucleotides. Avidin-conjugated nanomagnetic particles are washed over the array and allowed to couple to biotin molecules on the distal end of the oligonucleotides. The output of each nanomagnetic sensor is repeatedly monitored in the presence of a time-varying magnetic field gradient, and its average strength, as well as statistical measures of its variability and autocorrelation are recorded.

A sample containing mRNA fragments complementary to some of the oligonucleotide repeat sequences is incubated with the array, while an oscillating magnetic field gradient is applied to promote mass transfer. The array is washed, and the strength, variability and autocorrelation of the GMR sensors' output signals are again recorded in the presence of a time-varying magnetic field gradient. The array is washed at a higher temperature, and the GMR signals again recorded. Changes in the GMR signals of sensors bearing certain oligonucleotide sequences are interpreted as signaling the presence of mRNA fragments complementary to those sequences.

Example 5

Tethered Particle—Alter the Particle

Biotin-terminated poly(ethylene oxide) (PEO) chains are immobilized by washing onto an array of nanomagnetic sensors such that sensors bearing PEO chains carry an average of 1.01 chains. Nanomagnetic particles conjugated with a 1:20 molar ratio of streptavidin and a kinase substrate are washed over the array and allowed to couple to the biotin molecules on the distal end of the PEO chains. The output of each nanomagnetic sensor is repeatedly monitored, and its average strength, as well as statistical measures of its variability and autocorrelation are recorded. A minority of sensors are marked as giving anomalous results, and these sensors are neglected in subsequent analyses. An electrostatic field of 100 V/cm is applied roughly parallel to the surface of the array, and the output of each nanomagnetic sensor is repeatedly monitored, and its average strength, as well as statistical measures of its variability and autocorrelation are recorded.

A kinase capable of modifying the substrate on the nanoparticles is mixed with each member of a library of 1000 candidate kinase inhibitors, and each mixture is spotted onto 30 nanomagnetic sensors of the array, on average. The array is incubated at 37° C. for 2 hours, and then washed with a solution containing 0.1% of a non-ionic surfactant. An electrostatic field of 100 V/cm is applied roughly parallel to the surface of the array, and the output of each nanomagnetic sensor is repeatedly monitored, and its average strength, as well as statistical measures of its variability and autocorrelation are recorded. Reduced changes in the GMR signals of sensors which received certain kinase inhibitor candidates are interpreted as signaling the presence of effective kinase inhibitors.

Example 6

Sandwich Assay, Antibodies

Different portions of an array of 1,000 nanoscale GMR sensors are conjugated with five different monoclonal antibodies to ricin toxin. A sixth anti-ricin toxin antibody with an epitope not close to or overlapping with any of the others, and which binds more tightly than any of the others, is conjugated to superparamagnetic nanoparticles. Less than 20% of the particles bear more than 10 antibody molecules. A sample suspected of containing ricin toxin is applied to the sensor array through a microfluidic device, and the nanoparticles bearing the sixth antibody are allowed to bind to any toxin molecules on the array. After binding, a magnetic field is used to remove un-conjugated and mis-bound particles, bound particles are detected, and a stronger, ramping field is used to remove correctly-hybridized particles from the five immobilized antibodies. Particles are detected during this removal process, and binding which resists the lower field but is removed by a stronger field gradient characteristic of each of the five immobilized antibodies is interpreted as evidence of the presence of ricin toxin.

Example 7

Sandwich Assay, Micro RNA

A monoclonal RNA:DNA hybrid specific antibody is conjugated to superparamagnetic nanoparticles using aldehyde chemistry. microRNAs are isolated from a breast fine needle aspirate biopsy specimen, fragmented and exposed to an array of GMR sensors of which the majority bear a single DNA probe directed to target sequences potentially found in the miRNA. Non-active parts of the surface of the sensor array are covered with oligo-ethylene glycol chains by gold-thiol chemistry to suppress non-specific adsorption. The anti-RNA:DNA hybrid antibody-nanoparticle conjugate preparation is added to the sensor and allowed to bind. After particle binding, a magnetic field is used to remove un-conjugated and mis-bound particles, bound particles are detected, and a stronger field is used to remove correctly-bound particles. Particles are again detected, and hybridization which resists the lower field but not the stronger field is interpreted as evidence of the presence of specific miRNA sequences. The presence and absence of specific sequences is used to diagnose the patient's condition.

Example 8

High-Throughput Screening, Competitive, Simultaneous

An array of 150,000 GMR sensors is derivatized with a human cell surface protein implicated in the entry of hepatitis C virus. Baseline GMR signals are collected. A library of 5000 candidate viral entry inhibitors is prepared in a suspension of superparamagnetic nanoparticles bearing a Hepatitis C protein which interacts with the human cell surface protein, and each of the drug candidates is spotted onto the array, on an average of 20 sensors (of known locations) each. The array is washed, and GMR signals are collected from all sensors. Some sensors in locations known to have been spotted show 10-fold weaker signals than average. Drugs spotted onto at least three such sensors are further investigated as leads for a Hepatitis C viral entry inhibitor.

Example 9

Drinking Water Testing

A sample of water filtrate suspected of containing *Giardia* is exposed to a mixture of two different anti-*Giardia* monoclonal antibodies conjugated to two different superparamagnetic nanoparticles of different sizes. The sample is applied to the surface of a nanomagnetic sensor array with 200 nm GMR sensors separated by 150 nm. If clusters of superparamagnetic nanoparticles are observed, with size, shape and variations in intensity consistent with the two different antibodies both binding to *Giardia*, then the water is ruled unsafe for human consumption.

Example 10

Tethered Particle, Large Modification

Biotin-terminated poly(ethylene oxide) (PEO) chains are immobilized by washing onto an array of nanomagnetic sensors such that sensors bearing PEO chains carry an average of 1.01 chains. Nanomagnetic particles conjugated with a 1:20 molar ratio of streptavidin and an oligonucleotide are washed over the array and allowed to couple to the biotin molecules on the distal end of the PEO chains. The output of each nanomagnetic sensor is repeatedly monitored, and its average strength, as well as statistical measures of its variability and autocorrelation, are recorded. A minority of sensors are marked as giving anomalous results, and these sensors are neglected in subsequent analyses. An electrostatic field of 10 V/cm is applied roughly parallel to the surface of the array, and the output of each nanomagnetic sensor is repeatedly monitored, and its average strength, as well as statistical measures of its variability and autocorrelation are recorded.

An enzyme capable of modifying the oligonucleotide on the nanoparticles is mixed with each member of a library of 1000 candidate enzyme inhibitors, and each mixture is spotted onto 30 nanomagnetic sensors of the array, on average. The array is incubated at 37° C. for 2 hours, and then washed with a solution containing 0.1% of a non-ionic surfactant. An electrostatic field of 10 V/cm is applied roughly parallel to the surface of the array, and the output of each nanomagnetic sensor is repeatedly monitored, and its average strength, as well as statistical measures of its variability and autocorrelation, are recorded. Reduced changes in the GMR signals of sensors which received certain enzyme inhibitor candidates are interpreted as signaling the presence of effective enzyme inhibitors.

Example 11

Tethered Particle—Cut Tether

A set of oligodeoxynucleotides, whose sequences each include 8 copies of a particular 23-nucleotide sequence, are immobilized by spotting onto an array of nanomagnetic sensors. Each oligo is spotted onto 50 sensors, on average, and sensors bearing oligonucleotides carry an average of 1.05 oligonucleotides. Avidin-conjugated nanomagnetic particles are washed over the array and allowed to couple to biotin molecules on the distal end of the oligonucleotides. A magnetic field gradient is applied and removes some defectively-immobilized particles. The output of each nanomagnetic sensor is repeatedly monitored, and its average strength, as well as statistical measures of its variability and autocorrelation are recorded.

A sample containing oligonucleotides complementary to some of the oligonucleotide repeat sequences is incubated with the array, while an oscillating magnetic field gradient is applied to promote mass transfer. The array is washed, and a sample potentially containing a mixture of restriction endonucleases capable of cutting some of the double-stranded structures formed by hybridization of the soluble oligonucleotides with the immobilized oligonucleotides is applied to the array. A magnetic field gradient is applied, and removes some particles, and the strength, variability and autocorrelation of the GMR sensors' output signals are again recorded. Changes in the GMR signals of sensors bearing certain oligonucleotide sequences are interpreted as signaling the presence of oligonucleotides in the applied sample, complementary to those sequences.

It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed:

1. A sensor array comprising:
    a) a plurality of nanomagnetic sensing elements, wherein the sensing elements individually provide for less than 10 morphologically equivalent magnetization distribution states, by virtue of their nanometric size and corresponding nanomagnetic properties, and wherein electrical properties of said sensing elements vary in response to changes in applied magnetic environments, when such magnetic environments are applied; and b) molecular recognition elements associated with at least 0.001% of the nanomagnetic sensing elements.

2. The sensor array of claim 1, wherein the nanomagnetic sensing elements possess a shape that is topologically equivalent to that of a torus.

3. The sensor array of claim 1, wherein the nanomagnetic sensing elements possess a disk-like shape.

4. The sensor array of claim 1, wherein the nanomagnetic sensing elements possess a crescent-like shape.

5. The sensor array of claim 1, wherein the nanomagnetic sensing elements are in a shape of an n-sided polygon wherein the number of sides is less than 10000.

6. The sensor array of claim 1, wherein the molecular recognition elements reside closer than 100 nm to the center of the nanomagnetic sensing elements, and wherein, for those sensing elements containing molecular recognition elements, an average of no more than 5 such molecular recognition elements are associated with any one nanomagnetic sensing element within the array.

7. The sensor array of claim 1, wherein the molecular recognition elements reside in the center of the nanomagnetic sensing elements, and wherein, for those sensing elements containing molecular recognition elements, an average of no more than 5 such molecular recognition elements reside in the center of any one nanomagnetic sensing element within the array.

8. The sensor array of claim 2, wherein the ring-like nanomagnetic sensing elements, when viewed topologically, comprise an inner diameter of between 0.1 nm and 150 nm and a corresponding outer diameter of between 10 nm and 200 nm, and wherein the ring-like nanomagnetic sensing elements comprise a height of between 1 nm and 100 nm.

9. The sensor array of claim 1, wherein said array comprises at least 100 nanomagnetic sensing elements.

10. The sensor array of claim 1, wherein the nanomagnetic sensing elements comprise at least one nanomagnetic layer, wherein the local electrical properties of the sensing elements depend on local magnetization distribution.

11. The sensor array of claim 1, wherein the nanomagnetic sensing elements comprise a material selected from the group consisting of anisotropic magnetoresistive materials, giant magnetoresistive multilayers for current-in-plane configuration, giant magnetoresistive multilayers for current-perpendicular-to-plane configuration, tunneling magnetoresistive multilayers, ballistic magnetoresistive material, and combination thereof.

12. The sensor array of claim 1, wherein the nanomagnetic sensing elements comprise a material selected from the group consisting of materials exhibiting a Hall effect, materials exhibiting an extraordinary Hall effect, and combinations thereof.

13. The sensor array of claim 1, wherein the molecular recognition elements are selected from the group consisting of proteins, nucleic acids, nucleic acid analogs, sugars, and combinations thereof.

14. The sensor array of claim 1, wherein the molecular recognition elements are associated with the nanomagnetic sensing elements via chemical bonding.

15. The sensor array of claim 1, wherein the molecular recognition elements are bound to lithographically-defined binding areas.

16. The sensor array of claim 1, wherein the molecular recognition elements are bound to lithographically defined binding pads comprising gold, aluminum oxide, tantalum oxide, silicon oxide, and combinations thereof.

17. A system for sensing comprising:
  a) sensor array of claim 1;
  b) a population of superparamagnetic nanoparticles which are magnetizable into an unambiguously defined magnetic state using an applied magnetic field ranging from 1 Gauss to 5000 Gauss, wherein at least some of said superparamagnetic nanoparticles comprise biomolecular species covalently attached to their surface;
  c) a means for generating uniform magnetic fields; and
  d) a means for generating magnetic field gradients wherein at least some of biomolecular species on the superparamagnetic nanoparticles that comprise such species are capable of binding to at least some of the molecular recognition elements of the sensor array.

18. The system of claim 17, wherein said system is operable for applying force to manipulate and propagate superparamagnetic nanoparticles.

19. The system of claim 17, wherein the superpararnagnetic nanoparticles, in either a bound or unbound state, can be manipulated via magnetic fields.

20. The system of claim 17, wherein said system is operable for detection and quantitation of bio-molecular analytes.

21. The system of claim 17, further comprising a microfluidics device.

22. The system of claim 17, wherein the means for generating uniform magnetic fields involves a device selected from the group consisting of a conductor coil, a solenoid, a solenoid with a magnetic core, and combinations thereof.

23. The system of claim 17, wherein the binding between the biomolecular species and the molecular recognition elements comprises a linker species.

* * * * *

UNITED STATES PATENT AND TRADEMARK OFFICE
CERTIFICATE OF CORRECTION

PATENT NO. : 8,456,157 B2
APPLICATION NO. : 11/996945
DATED : June 4, 2013
INVENTOR(S) : Litvinov et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1525 days.

Signed and Sealed this
Eighth Day of September, 2015

Michelle K. Lee
*Director of the United States Patent and Trademark Office*